United States Patent
Nagy et al.

[11] Patent Number: 5,814,310
[45] Date of Patent: Sep. 29, 1998

[54] MONOHYDRIC ALCOHOL-FREE COSMETIC STICK

[75] Inventors: Adrienne Nagy, Waldwick, N.J.; Joanne Leaver, Selden, N.Y.; Steven Messin, Plainview, N.Y.; Donna Meningall, Baldwin, N.Y.

[73] Assignee: E-L Management Corp, New York, N.Y.

[21] Appl. No.: 788,140

[22] Filed: Jan. 24, 1997

[51] Int. Cl.[6] .............................. A61K 7/32; A61K 7/06; A61K 7/00
[52] U.S. Cl. ........................... 424/65; 424/70.1; 424/400; 424/401; 424/DIG. 5
[58] Field of Search ..................... 424/400, 401, 424/65, 70.1, DIG. 5

[56] References Cited

U.S. PATENT DOCUMENTS

| | | | |
|---|---|---|---|
| 2,890,987 | 6/1959 | Hilfer | 424/68 |
| 4,252,789 | 2/1981 | Broad | 424/65 |
| 4,268,498 | 5/1981 | Gedeon et al. | 424/59 |
| 4,725,430 | 2/1988 | Schamper et al. | 424/66 |
| 4,759,924 | 7/1988 | Luebbe et al. | 424/42 |
| 5,120,541 | 6/1992 | Macaulay et al. | 424/401 |
| 5,128,123 | 7/1992 | Brewster et al. | 424/65 |
| 5,336,497 | 8/1994 | Guerrero et al. | 424/401 |
| 5,407,668 | 4/1995 | Kellner | 424/65 |
| 5,462,736 | 10/1995 | Rech et al. | 424/401 |

FOREIGN PATENT DOCUMENTS 0 450 597 B1  10/1996  Germany.

*Primary Examiner*—Shelley A. Dodson
*Attorney, Agent, or Firm*—Dorene M. Price, Esq.; Karen A. Lowney, Esq.

[57] ABSTRACT

The present invention relates to a clear cosmetic stick composition comprising (a) from about 3–15% of a soap gelling agent; (b) from about 10–90% of at least one polyhydric alcohol solvent; and (c) from about 0.5–10% of a combination of the clarifying agents pentadoxynol 200 and ethoxylated jojoba esters. The composition is useful, for example, as the base for a deodorant stick.

26 Claims, No Drawings

MONOHYDRIC ALCOHOL-FREE COSMETIC STICK

FIELD OF THE INVENTION

The present invention relates to cosmetic compositions, in particular, solid stick compositions. More specifically, the invention relates to clear, non-irritating, alcohol-free cosmetic sticks.

BACKGROUND OF THE INVENTION

A number of characteristics have recently become important to consumers in the purchase of deodorant sticks. One aspect which is very desirable to purchasers is a clear deodorant stick, which will not leave a white residue on skin or clothing. However, the preparation of a completely clear stick is not a simple matter, as the sticks are commonly prepared with a soap gelling agent, such as sodium stearate, which has a tendency to crystallize, and therefore mar the appearance of the product. An additional issue is the elimination of monohydric alcohols, particularly short chain alcohols, such as ethyl or isopropyl alcohol, from the preparation. Though historically a frequent component of deodorant sticks, primarily as a solvent for the gelling agents, these materials have fallen into disfavor recently because of their volatility, and have been heavily regulated in some states. In addition to environmental concerns, however, there is a purely practical advantage to preparation of an alcohol-free stick: the presence of volatile alcohols in the composition causes the stick to shrink away from the sides of container over time, due to the evaporation of the alcohol. Polyhydric alcohols provide a suitable substitute for the monohydric alcohols, as they are less volatile; however, at the high levels at which they are typically used, they tend to be irritating to the user. A number of clear or transparent cosmetic sticks have previously been disclosed, for example, in U.S. Pat. Nos. 5,462,736; 5,407,668; 4,268,498; 4,759,924; 5,120,541; 5,128,123; 4,252,789; 4,725,430; 2,890,987; and EP 450597. Notwithstanding the foregoing, however, there continues to be a demand for non-irritating, alcohol-free cosmetic sticks with exceptional clarity and stability. The present invention provides such a cosmetic stick.

SUMMARY OF THE INVENTION

The present invention relates to a clear cosmetic stick composition comprising (a) from 3–15% of a soap gelling agent; (b) from about 10–90% of at least one polyhydric alcohol solvent; and (c) from about 0.5–10% of a combination of the clarifying agents pentadoxynol 200 and an ethoxylated jojoba oil. The cosmetic stick of the invention can be used as a base for any type of cosmetic in which a transparent stick is desirable. In a preferred embodiment, the stick is used as a base for a deodorant composition.

DETAILED DESCRIPTION OF THE INVENTION

The sticks of the present invention are rendered solid by the use of a soap as a gel-forming agent. For the present purposes, the appropriate soaps used as gelling agents are low molecular weight amine and alkali metal salts, such as sodium and potassium, of fatty acids. In a preferred embodiment, the soap gelling agent is selected from sodium, potassium or amine salt of a C12–C22 fatty acid. Such gelling agents are known in the art, and are described, for example, in U.S. Pat. No. 5,128,123, the contents of which are incorporated herein by reference. In a particularly preferred embodiment, the gelling agent is a salt of stearic acid, and most preferably is sodium stearate. The gelling agent is preferably present in an amount of from about 3–15%, more preferably from about 5–10%.

In order to prepare the final composition, the gelling agent must be solubilized. To achieve solubilization of the soap, at least one polyhydric alcohol is used. Strictly speaking, a large variety of polyhydric alcohols are capable of being used as solvents for the gelling agent; it is preferred that the polyhydric alcohol be a C2–C6 alcohol, containing from 2–6 hydroxyl groups. Preferably, the alcohol solvent is present in an amount of from about 10–90% of the stick, more preferably, from about 40–70%. Particularly preferred is propylene glycol, or any combination of propylene glycols, for example a combination of propylene glycol and dipropylene glycol; in a particularly preferred embodiment, the solvent comprises from about 1–10%, more preferably about 3–8%, of dipropylene glycol, and about 10–80%, more preferably about 30–65% of propylene glycol. Other glycols, such as butylene glycol, will solubilize the gelling agent, but if used in large amounts, will interfere with proper gelling. If other such polyhydric alcohols are to be used, they should be used in small amounts, i.e., no more than 5% of the total amount of polyhydric alcohol.

The stick of the present invention also contains a combination of clarifying agents. In a particularly preferred embodiment, the clarifying agents employed are pentadoxynol-200 (available under the tradename CLARIT PDP-200 from RTD Chemicals Corp., Hackettstown, N.J.) and a highly ethoxylated jojoba oil, or esters. The latter is prepared by standard chemical reactions, by first saponifying jojoba oil to liberate the fatty alcohols and fatty acids that form the natural jojoba ester, and then adding ethylene oxide to the hydroxyl group of the fatty alcohol and the carboxylic group on the fatty acid. In a preferred embodiment, 120 ethylene oxide units are added per mole of jojoba oil. Such a product is commercially available from Floratech (Gilbert, Ariz.) as Florasolve Jojoba PEG-120.

The total amount of combined clarifying agents in the formulation can be from about 0.5–10% by weight, preferably from about 1–8%. Individually, the clarifying agents are preferably present in an amount of from about 0.25–3% ethoxylated jojoba, and 1–5% pentadoxynol-200. The amounts of the clarifying agents can also be varied in accordance with the amount of sodium stearate used. For example, larger amounts of sodium stearate can be balanced with lower amounts of pentadoxynol 200. It is interesting to note that both of the clarifying agents used in the present formulation are highly ethoxylated; such materials tend to be irritating on the skin. It is surprising, then, that the product resulting from the combination of these two agents produces relatively little irritation when applied to the skin. While not wishing to be bound by any particular theory, the use of the jojoba esters, a naturally occurring product, may be an important factor in avoiding the level of irritation normally seen with other ethoxylated materials.

The remainder of the stick can be made up primarily with water, which will typically be from about 10–60% by weight of the total composition. However, more commonly, the clear stick optionally contains one or more other components which assist in retaining clarity and/or feel of the stick. For example, to enhance clarity, it may desirable to incorporate an alkanolamide, particularly a fatty acid alkanolamide, such as stearamide DEA or MEA, cocamide DEA or MEA, myristamide DEA or MEA, lauramide DEA or MEA, tallamide DEA or MEA, and the like. A preferred alkanolamide is stearamide DEA. Other known clarifying enhancers include, for example, stearyl alcohol and sodium chloride; these compounds also assist in reducing "sweating" on the surface of the stick.

The stick may also include emollients, such as vegetable oils, e.g., coconut oil, corn oil, sunflower oil, palm oil, soybean oil; carboxylic acid esters, e.g., isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, or cholesterol; glyceryl esters, such as glyceryl stearate, glyceryl dioleate, glyceryl distearate, glyceryl linoleate, glyceryl myristate; or silicone oils, e.g., dimethicone, dimethiconol, dimethicone copolyol, phenyl trimethicone, methicone, simethicone, cyclomethicone; and nonvolatile hydrocarbons, such as isoparaffins, squalane, or petrolatum. A preferred emollient is dimethicone copolyol. The emollient is preferably present in an amount of from about 1–10%, but may vary depending upon the intended end use of the stick.

Depending upon the intended end use, the stick may also comprise one or more "active" ingredients. For example, the stick may be used as the base for a sunscreen, and therefore may contain any known sunscreen agent, such as p-aminobenzoic acid, benzophenone, a cinnamic acid ester, and the like. The stick may also function as a fragrance applicator, and in such a case the active component would be one or more fragrance components. The stick can also be used to deliver skin conditioning or therapeutic actives, such as retinoids, antioxidants, alpha or beta-hydroxy acids, ceramides, antibiotics, antiinflammatories, antiirritants, and the like. The amount of any active used in combination with the stick of the invention will be in accordance with its ordinary topical use, and can thus be readily be determined by one of ordinary skill.

In a preferred embodiment, the stick is an underarm deodorant stick. In this embodiment, the active material will constitute one or more deodorant compounds, for example aluminum chlorhydrate, aluminum zirconium tetrachlorohydrate, hexachlorophene, zinc phenolsulfonate, chloroxylenol, triclosan, and the like. It should be noted that, when sodium stearate is the gelling agent, it is preferred that the metallic deodorant salts not be used in combination with it. In a preferred embodiment, in keeping with the non-irritating character of the stick, a "natural" deodorant is used. This includes, for example, lichen extract, tea tree oil or enzymatic deodorizing agents. Again, the amount of deodorant compound used is dependent upon the compound, and is determined in accordance with its ordinary usage.

It has also been found that the stick benefits from the addition of a small amount, e.g., from 0.01–0.1% of sodium metabisulfite. This ingredient is useful in preventing darkening of the stick, which darkening may result from oxidation of natural ingredients, such as the deodorant or fragrance, in the formulation.

The stick of the present invention has a number of advantageous characteristics. It is surprisingly non-irritating, given the number of typically irritating materials which are used in the formulation. Moreover, the stick is very stable, and undergoes very little shrinkage over time. In addition, the stick is unexpectedly capable of accepting relatively large amounts of fragrance without any loss of clarity. Although most currently available sticks employ only small amounts, i.e., less than 0.5%, of fragrance, the present stick can accommodate at least up to 2% of fragrance, with no affect on the stick's appearance. This makes the stick particularly well adapted for use as a fragrance applicator, as well as a fragranced deodorant stick.

The invention is further illustrated by the following non-limiting example.

EXAMPLES

Example 1

The following is exemplary of a clear deodorant stick of the invention:

| MATERIAL | WEIGHT % |
|---|---|
| Propylene glycol | 65.00 |
| water | QS |
| sodium stearate | 7.00 |
| dimethicone copolyol | 2.00 |
| pentadoxynol-200 | 2.50 |
| sodium chloride | 1.50 |
| propylene glycol/lichen extract | 2.00 |
| Jojoba PEG-120 (Florasolve) | 1.50 |
| stearamide DEA | 0.75 |
| stearyl alcohol | 0.30 |
| sodium metabisulfite | 0.03 |

What we claim is:

1. A clear cosmetic stick composition comprising (a) from about 3–15% of a soap gelling agent; (b) from about 10–90% of at least one polyhydric alcohol solvent; and (c) from about 0.5–10% of a combination of the clarifying agents pentadoxynol 200 and ethoxylated jojoba esters.

2. The composition of claim 1 in which the soap gelling agent is a sodium, potassium or amine salt of a C12–C22 fatty acid.

3. The composition of claim 1 in which the polyhydric alcohol solvent comprises propylene glycol.

4. The composition of claim 1 in which the polyhydric alcohol solvent comprises both propylene glycol and dipropylene glycol.

5. The composition of claim 1 in which the jojoba ester is jojoba PEG-120 esters.

6. The composition of claim 1 which also comprises from about 0.1–5% of an alkanolamide clarifying enhancer.

7. The composition of claim 6 in which the alkanolamide is a fatty acid alkanolamide.

8. The composition of claim 1 which also comprises a deodorant.

9. The composition of claim 1 which also comprises a fragrance.

10. The composition of claim 1 which also comprises from about 0.01–0.1% of sodium metabisulfite.

11. A clear cosmetic stick composition comprising (a) from about 3–15% of a C12–C22 fatty acid salt gelling agent; (b) from about 10–90% of a C2–C6 polyhydric alcohol solvent; and (c) from about 0.5–10% of a combination of the clarifying agents pentadoxynol 200 and ethoxylated jojoba esters.

12. The composition of claim 11 which comprises from about 5–10% of the gelling agent, about 40–70% of a polyhydric alcohol solvent; and from about 1–8% of the combination of clarifying agents.

13. The composition of claim 12 in which the gelling agent is sodium stearate.

14. The composition of claim 12 in which the alcohol solvent comprises both propylene glycol and dipropylene glycol, in amounts of from about 10–80% and 1–10%, respectively.

15. The composition of claim 12 which comprises from about 0.1–5% of a fatty acid alkanolamide clarifying enhancer.

16. The composition of claim 15 in which the clarifying enhancer is stearamide DEA.

17. The composition of claim 12 in which the jojoba ester is jojoba PEG-120 esters.

18. The composition of claim 12 which also comprises from 0.01–0.1% of sodium metabisulfite.

19. A clear cosmetic stick composition comprising (a) from about 3–15% of sodium stearate; (b) from about 10–90% of a propylene glycol; and (c) from about 0.5–10% of a combination of the clarifying agents pentadoxynol 200 and jojoba oil PEG-120 esters.

20. The composition of claim 19 comprising (a) from 5–10% sodium stearate; (b) from about 40–70% of a propylene glycol; and (c) from about 1–5% of pentadoxynol 200 and from about 0.25–3% of jojoba PEG-120 esters.

21. The composition of claim 20 in which (b) comprises both propylene glycol and dipropylene glycol, in amounts of from about 30–65% and 3–8%, respectively.

22. The composition of claim 21 which also comprises from about 1–5% of stearamide DEA.

23. The composition of claim 22 which also comprises a deodorant.

24. The composition of claim 22 which also comprises from about 0.5 to 2% of fragrance.

25. The composition of claim 23 which also comprises an emollient.

26. The composition of claim 23 which also comprises from about 0.01–0.1% of sodium metabisulfite.

* * * * *